United States Patent
Lai et al.

(10) Patent No.: US 10,968,159 B1
(45) Date of Patent: Apr. 6, 2021

(54) METHOD FOR MANUFACTURING TEREPHTHALIC ACID

(71) Applicant: Far Eastern New Century Corporation, Taipei (TW)

(72) Inventors: Po-Chen Lai, Taoyuan (TW);
Jyun-Sian Lee, Taoyuan (TW);
Sih-Hao Chiang, Taoyuan (TW);
Chin-Shui Liang, Taoyuan (TW);
Hsiang-Chin Tsai, Taoyuan (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 0 days.

(21) Appl. No.: 16/831,052

(22) Filed: Mar. 26, 2020

(30) Foreign Application Priority Data

Sep. 26, 2019 (TW) .................................. 108134935

(51) Int. Cl.
*C07C 51/43* (2006.01)
*C07C 51/02* (2006.01)
*C07C 63/26* (2006.01)

(52) U.S. Cl.
CPC .............. *C07C 51/43* (2013.01); *C07C 51/02* (2013.01); *C07C 63/26* (2013.01)

(58) Field of Classification Search
None
See application file for complete search history.

(56) References Cited

U.S. PATENT DOCUMENTS 3,102,137 A * 8/1963 Wise ................... C07C 51/487
562/480
2003/0225299 A1 12/2003 Yazaki et al.

FOREIGN PATENT DOCUMENTS

| CN | 101503353 | | 5/2012 |
| CN | 105753687 | * | 7/2016 |
| TW | I322803 B | | 4/2010 |
| TW | I328002 B | | 8/2010 |
| TW | 201811726 A | | 4/2018 |

OTHER PUBLICATIONS https://www.filterbag.com/U-S-Mesh-vs-Micron-21.html, downloaded on Sep. 25, 2020 (Year: 2020).*
Extended European Search Report dated Nov. 2, 2020 from related Application No. 20175253.2.

* cited by examiner

*Primary Examiner* — Amy C Bonaparte
(74) *Attorney, Agent, or Firm* — Fay Sharpe LLP

(57) ABSTRACT

Method for manufacturing terephthalic acid includes following steps: providing a titrant receptor solution, the titrant receptor solution being water; adding disodium terephthalate aqueous solution and an acid titrant into the titrant receptor solution to form terephthalic acid crystals and an end-point solution, and separating the terephthalic acid crystals from the end-point solution.

8 Claims, 2 Drawing Sheets

METHOD FOR MANUFACTURING TEREPHTHALIC ACID

RELATED APPLICATIONS

This application claims priority to Taiwan Application Serial Number 108134935, filed Sep. 26, 2019, which is herein incorporated by reference.

BACKGROUND

Polyester has excellent mechanical strength and chemical stability, so it has been widely used in various applications. However, because the compositions of different products are different, and the additives of different products are also different, the difficulty of recycling polyester in different products has risen.

In the recycling of polyethylene terephthalate products, one of the recycling stages is the formation of terephthalic acid crystals. However, the particle size of the terephthalic acid crystals formed by using the current technology is too small (for example, about 10 μm), which increases the difficulty of subsequent processing for recycling. In general, the particle size of terephthalic acid crystals used in industry needs to be greater than 30 μm in order to provide better processing quality. Thus, a novel method for manufacturing terephthalic acid is urgently needed to solve the above problems.

SUMMARY

According to one aspect of the present disclosure, a method for manufacturing terephthalic acid includes following steps: providing a titrant receptor solution, the titrant receptor solution being water; adding disodium terephthalate aqueous solution and an acid titrant into the titrant receptor solution to form terephthalic acid crystals and an end-point solution, and separating the terephthalic acid crystals from the end-point solution.

In some embodiments, in the process of adding the disodium terephthalate aqueous solution and the acid titrant into the titrant receptor solution to form the terephthalic acid crystals and the end-point solution, a pH value of the titrant receptor solution is in a range of 1.0-3.5.

In some embodiments, the disodium terephthalate aqueous solution and the acid titrant are added into the titrant receptor solution to form the terephthalic acid crystals and the end-point solution, a temperature of the titrant receptor solution is in a range of 50° C.-90° C.

In some embodiments, a pH value of the end-point solution is in a range of 1.0-3.5.

In some embodiments, seed crystals are added into the titrant receptor solution before adding disodium terephthalate aqueous solution and the acid titrant into the titrant receptor solution.

In some embodiments, the seed crystals are terephthalic acid.

In some embodiments, basing on 100 parts by weight of disodium terephthalate of the disodium terephthalate aqueous solution, the seed crystals are 0.05 to 0.2 parts by weight.

In some embodiments, the acid titrant is dilute sulfuric acid aqueous solution.

In some embodiments, a weight percentage concentration of the dilute sulfuric acid aqueous solution is in a range of 10%-50%.

In some embodiments, a median particle size $Dv_{50}$ of the terephthalic acid crystals is in a range of 70-150 μm.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
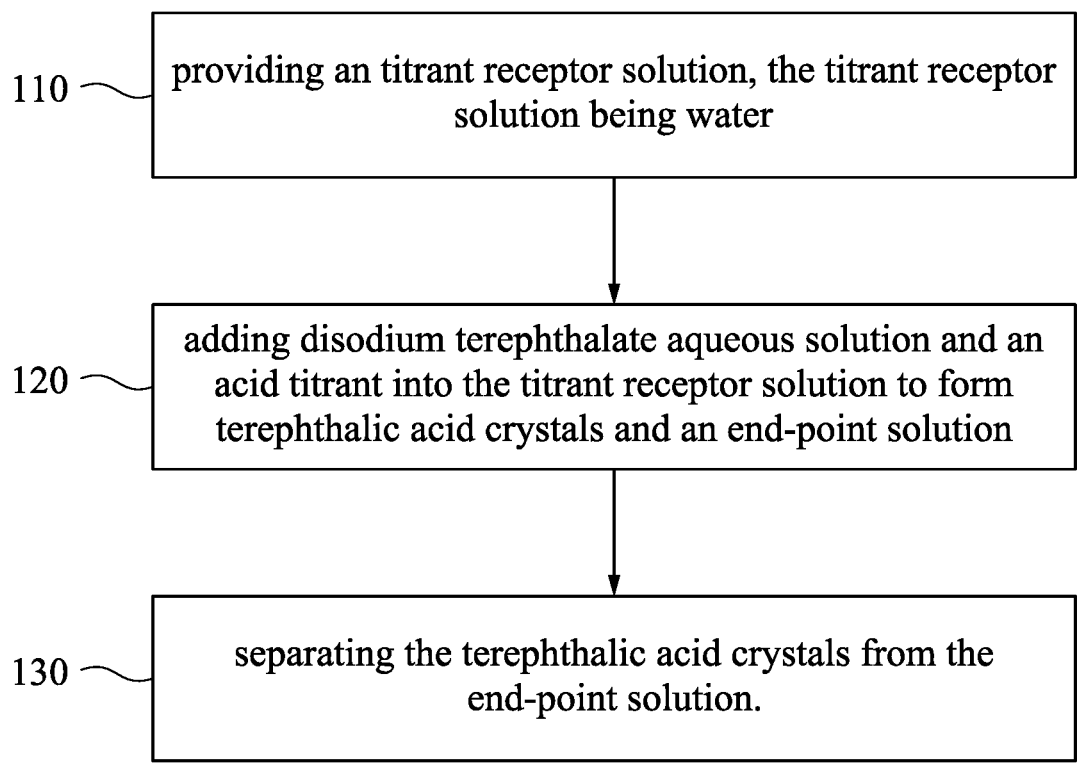
FIG. 1 is a flowchart illustrating a method 100 for manufacturing terephthalic acid according to some embodiments of the present invention.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

As used herein, the singular word includes the plural reference object unless there is another clear reference in the content. By referring to a specific reference such as "an embodiment", in at least one of the embodiments disclosed in this disclosure, it represents a specific feature, structure, or characteristic. When a word appears through a special reference, it is not necessary to refer to the same embodiment. Furthermore, in one or more embodiments, these special features, structures, or characteristics can be combined with each other as appropriate.

The present invention provides a method for manufacturing terephthalic acid. Please refer to FIG. 1, which is a flowchart illustrating a method 100 for manufacturing terephthalic acid according to some embodiments of the present invention.

Referring to step 110, a titrant receptor solution is provided, in which the titrant receptor solution is water. The description "the titrant receptor solution is water" herein means that the titrant receptor solution includes water or the titrant receptor solution consists essentially of water. In other words, in some embodiments, the titrant receptor solution may contain ingredients other than water.

In some embodiments, seed crystals are presented in the titrant receptor solution. With the addition of structured crystals, the molecules in the solution can easily interact with each other, without being excessively dependent on the random flow. In the solution, the phase change of transforming the solute into a crystal lattice is called nucleation. In other words, the effect of adding seed crystals is to shorten the time to nucleation during crystallization. Thus, adding seed crystals makes it easier to form terephthalic acid crystals in subsequent steps of manufacturing process, and the particle size of the formed terephthalic acid crystals becomes larger. In some embodiments, the seed crystals are terephthalic acid. In other words, by adding a small amount of commercial terephthalic acid, the overall process speed can be accelerated, and the quality of produced terephthalic acid crystals is better.

Next, referring to step 120, disodium terephthalate aqueous solution and acid titrant are added into the titrant receptor solution to form terephthalic acid crystals and an end-point solution. In this step, it is noted that the disodium terephthalate aqueous solution and the acid titrant are respectively (i.e., independently) added to the titrant receptor solution concurrently. In some embodiments, the disodium terephthalate aqueous solution and the acid titrant are injected into the titrant receptor solution by using two peristaltic pumps. In detail, the present invention applies a two-column titration method.

In some embodiments, the disodium terephthalate aqueous solution includes pure water and disodium terephthalate. In some embodiments, the weight percentage of the disodium terephthalate aqueous solution is 2 wt % to 10 wt %, for example, 3 wt %, 5 wt %, 7 wt %, or 9 wt %.

In some embodiments, in the process of adding the disodium terephthalate aqueous solution and the acid titrant into the titrant receptor solution, a pH value of the titrant receptor solution is maintained in the range of 1.0-3.5, for example, 1.5, 2.0, 2.5, or 3.0. In some embodiments, firstly the acid titrant is added into the titrant receptor solution until the pH of the titrant receptor solution reaches in the range of 1.0-3.5. Thereafter, the disodium terephthalate aqueous solution and acid titrant both are added into the titrant receptor solution while the pH value of the titrant receptor solution is maintained in the range of 1.0-3.5. By controlling the pH value of the titrant receptor solution in the mentioned range, terephthalic acid crystals are formed with better quality in the present invention, for example, terephthalic acid crystals formed with larger particle size. Since the present invention uses a two-column titration method, the pH value of the titrant receptor solution can be controlled more accurately. In certain embodiments, the pH value of the end-point solution is in the range of 1.0-3.5, for example, 1.5, 2.0, 2.5 or 3.0. It should be understood that the end-point solution herein refers to a state where the reactant (disodium terephthalate) is completely reacted. During the titration, if the pH value of the titrant receptor solution is lower than 1.0 or higher than 3.5, or the pH value of the end-point solution is lower than 1.0 or higher than 3.5, the purity of the formed terephthalic acid crystals is lower.

The flow rates and the concentrations of the disodium terephthalate aqueous solution (basic) and the acid titrant (acidic) of the present invention need to be matched with each other to maintain the pH of the titrant receptor solution in a specific range. For example, the flow rate of the disodium terephthalate aqueous solution is in the range of 5-10 ml per minute, such as 6 ml, 7 ml, 8 ml or 9 ml per minute. The flow rate of the acid titrant is ranged from 1 to 5 ml per minute, for example, 2 ml, 3 ml or 4 ml per minute. The flow rates mentioned above are only exemplary, and they could be varied according to the usage (amounts) of disodium terephthalate aqueous solution and acid titrant and the types of acid titrant. In large-scale mass production, the flow rates of disodium terephthalate aqueous solution and acid titrant may be raised to several liters per minute. In some embodiments, the time period of titration completion is about 1-8 hours, for example, 2 hours, 3 hours, 4 hours, 5 hours, 6 hours, or 7 hours. If the time period of titration completion is less than 1 hour, the particle size of the formed terephthalic acid crystals becomes smaller. If the time period of titration completion is more than 8 hours, the overall process time will be too long, which will unfavorably affect the production efficiency.

It is noted that if the pH value of titrant receptor solution exceeds the mentioned range during the process of titration, such as greater than 3.5 or less than 1.0, the particle size of the formed terephthalic acid crystals becomes smaller.

Further, in some embodiments, disodium terephthalate aqueous solution and acid titrant are added into the titrant receptor solution at a temperature in a range of 50° C.-90° C., for example, 60° C., 70° C., or 80° C. In some embodiments, the temperature of the titrant receptor solution is in the range of 50° C.-90° C. when adding disodium terephthalate aqueous solution and acid titrant into the titrant receptor solution, for example, 60° C., 70° C., or 80° C. By controlling the temperature of the titrant receptor solution within the range mentioned above, the quality of the formed terephthalic acid crystals is better, for example, terephthalic acid crystals formed with larger particle size.

In some embodiments, the acid titrant is dilute sulfuric acid aqueous solution. In some embodiments, the weight percentage concentration of the dilute sulfuric acid aqueous solution can be in the range of 10-50%, for example, 20%, 30%, or 40%.

Referring to step 130, the terephthalic acid crystals are separated from the end-point solution. Since terephthalic acid crystals are difficult to be dissolved in the end-point solution, any solid-liquid separation method can be used. In some embodiments, gravity filtration or decompression filtration can be used (that is, filtration is assisted by gravity or decompression).

In some embodiments, the median diameter $Dv_{50}$ of the terephthalic acid crystals is in the range of 70-200 μm. In some embodiments, the median diameter $Dv_{50}$ of the terephthalic acid crystals is greater than 70 μm, such as 75 μm, 80 μm, 85 μm, or 90 μm. As mentioned above, in general, the particle size of terephthalic acid crystals used in industry needs to be greater than 30 μm in order to provide better processing quality. Therefore, the terephthalic acid crystal formed by the present invention can be directly used in subsequent processing applications without additional steps such as recrystallization. In some embodiments, the median diameter $Dv_{50}$ of the terephthalic acid crystals is less than 150 μm, for example, 140 μm, 130 μm, 120 μm, 110 μm, or 100 μm.

Some examples and comparative examples of the present invention are exemplarily described below. It should be understood that the following examples are illustrative and therefore are not intended to limit the embodiments of the present invention.

Example 1

50 grams of disodium terephthalate (Alfa Aesar™, 99+%) was added into 1000 grams of pure water to form disodium terephthalate aqueous solution. Further, 60 grams of 40% dilute sulfuric acid aqueous solution was formulated, and 800 grams of pure water was prepared as the titrant receptor solution. Thereafter, 0.05 grams of terephthalic acid was added into the water (the titrant receptor solution), and the titrant receptor solution was slowly stirred by using a stirrer at a temperature of 50° C.-90° C. The disodium terephthalate aqueous solution and the dilute sulfuric acid aqueous solution were dripped into the titrant receptor solution, and the titration flow rates of the disodium terephthalate aqueous solution and the dilute sulfuric acid aqueous solution were controlled by peristaltic pumps. The flow rate of the disodium terephthalate aqueous solution was 8 ml per minute, and the flow rate of the dilute sulfuric acid aqueous solution was in the range of 1.5-3.5 ml per minute, in such the pH of the titrant receptor solution was controlled within the range of 1.0-3.5. During the titration, terephthalic acid slowly precipitates. When the disodium terephthalate aqueous solution was used up, the end point of the titration was reached. Thereafter, the terephthalic acid and the titrant receptor solution were separated by suction filtration, and the particle size was measured by using a laser particle size analyzer.

Comparative Example 1

The 50 grams of disodium terephthalate (Alfa Aesar™, 99+%) and 0.05 grams of terephthalic acid were added into 1000 grams of pure water to form disodium terephthalate aqueous solution. Further, 60 grams of 40% dilute sulfuric acid aqueous solution was formulated. Thereafter, the disodium terephthalate aqueous solution (the titrant receptor solution) was slowly stirred by using a stirrer at a temperature of 60° C. The dilute sulfuric acid aqueous solution was dripped into the titrant receptor solution, and the titration flow rate of the dilute sulfuric acid aqueous solution was controlled by a peristaltic pump. The flow rate of dilute sulfuric acid aqueous solution was 0.3 ml per minute. During the process of titration, terephthalic acid slowly precipitates. The end of the titration was reached when the pH value of the titrant receptor solution was in the range of 1.0-3.5. Thereafter, the terephthalic acid and the titrant receptor solution were separated by suction filtration, and the particle size was measured by using a laser particle size analyzer.

Table 1 shows the $Dv_{10}$, $Dv_{50}$, $Dv_{90}$ and time period of titration completion of the formed terephthalic acid crystals of Example 1 and Comparative Example 1, in which $Dv_{10}$ represents a value that 10% of terephthalic acid crystals in diameter less than or equal to this value, $Dv_{50}$ represents a value that 50% of terephthalic acid crystals in diameter less than or equal to this value, $Dv_{90}$ represents a value that 90% of terephthalic acid crystals in diameter less than or equal to this value.

TABLE 1

| | Example 1 | Comparative Example 1 |
|---|---|---|
| $Dv_{10}$ | 34.7 | 5.27 |
| $Dv_{50}$ (median particle size, μm) | 75.5 | 38.8 |
| $Dv_{90}$ | 173.3 | 262.8 |
| time period of titration completion (sec) | 22 | 42 |

As shown in Table 1, the median particle size $Dv_{50}$ of Example 1 is 75.5 μm, which is much larger than median particle size $Dv_{50}$ of Comparative Example 1. The method disclosed in the present invention indeed obtains terephthalic acid crystals with larger particle size. Further, the particle size distribution of Example 1 is more concentrated while the particle size distribution of Comparative Example 1 is more dispersed according to $Dv_{10}$, $Dv_{50}$ and $Dv_{90}$. In subsequent applications, a broader distribution of particle size results in difficulties of processing. Accordingly, terephthalic acid crystals formed by using the method of present invention are favorable for the subsequent processing.

Further, the time period of titration completion of Example 1 was only half to that of Comparative Example 1. Because the particle size of the formed terephthalic acid crystals in Comparative Example 1 was relatively smaller, the density of a filter cake generated during filtration was high, which affected the time period of titration completion. Comparing to Comparative Example 1, the method of the present invention can increase the particle size by nearly two times, and the filtration time was shortened by about 52% under the same amount of filtration.

It is noted that the pH value of Example 1 was maintained in the range of 1.0-3.5 during the titration. However, the titrant receptor solution of Comparative Example 1 was disodium terephthalate aqueous solution, thus initially the titrant receptor solution was alkaline (e.g. pH value is about 8). With the acid titrant was added into the titrant receptor solution, the pH value of the titrant receptor solution decreased to a level of 1.0-3.5 and the end of the titration was reached. As it's observed in Example 1 and Comparative Example 1, the pH value during the process of titration certainly affects the particle size of the terephthalic acid crystals.

Figure 2:
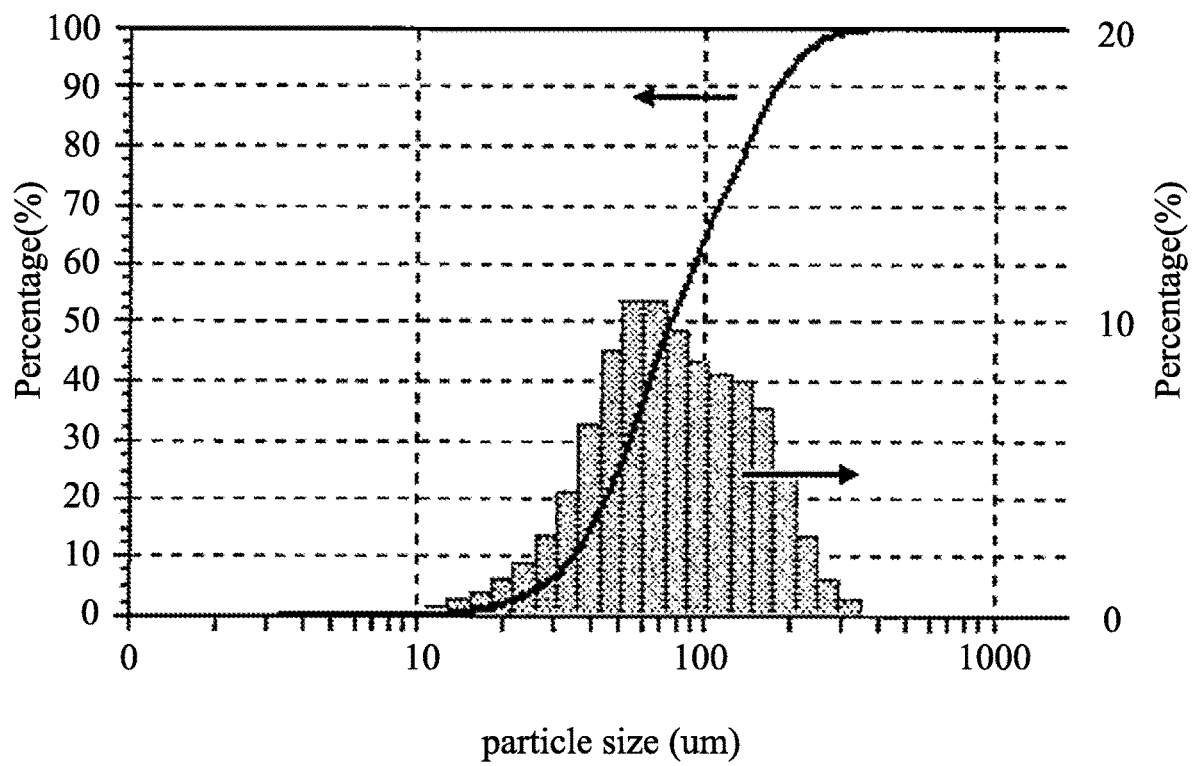
FIG. 2 is a diagram showing particle size distribution of the terephthalic acid crystals according to Example 1 of the present invention.

Please refer to FIG. 2, which is a diagram showing particle size distribution of the terephthalic acid crystals according to Example 1 of the present invention. In FIG. 2, the curve is the cumulative percentage corresponding to the vertical axis on the left. The bar graph is the percentage of each particle size corresponding to the vertical axis on the right. As shown in FIG. 2, the particle size distribution of the terephthalic acid crystals of the present invention is similar to Gaussian distribution, which is beneficial for subsequent processing. In addition, nearly 40% of the terephthalic acid crystals of Example 1 were formed with particle size greater than 100 μm, which substantially increased the usability of the terephthalic acid crystals.

The method for manufacturing terephthalic acid provided by the present invention can substantially increase the particle size of the formed terephthalic acid crystals, so that the formed terephthalic acid crystals can be directly used for subsequent processing. It is noted that disodium terephthalate aqueous solution and acid titrant were added to titrant receptor solution by using the double column titration in the present invention, thus it is possible to accurately control the pH value of the titrant receptor solution during titration process. Because the pH value of the titration process is maintained in a specific range, the median diameter of the formed terephthalic acid crystals can be greater than 75 μm.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for manufacturing terephthalic acid, comprising:
   providing a titrant receptor solution, wherein the titrant receptor solution includes water, and a pH value of the titrant receptor solution is in a range of 1.0-3.5;
   adding a disodium terephthalate aqueous solution and an acid titrant into the titrant receptor solution to form terephthalic acid crystals and an end-point solution, wherein a pH value of the titrant receptor solution is in a range of 1.0-3.5; and
   separating the terephthalic acid crystals from the end-point solution, wherein a pH value of the end-point solution is in a range of 1.0-3.5.

2. The method of claim 1, wherein in the process of adding the disodium terephthalate aqueous solution and the acid titrant into the titrant receptor solution to form the terephthalic acid crystals and the end-point solution, a temperature of the titrant receptor solution is in a range of 50° C.-90° C.

3. The method of claim 1, further comprising:
   adding seed crystals into the titrant receptor solution before adding the disodium terephthalate aqueous solution and the acid titrant into the titrant receptor solution.

4. The method of claim 3, wherein the seed crystals are terephthalic acid.

5. The method of claim 3, wherein based on 100 parts by weight of disodium terephthalate of the disodium terephthalate aqueous solution, the seed crystals are 0.05 to 0.2 parts by weight.

6. The method of claim 1, wherein the acid titrant is a dilute sulfuric acid aqueous solution.

7. The method of claim 6, wherein a weight percentage concentration of the dilute sulfuric acid aqueous solution is in a range of 10%-50%.

8. The method of claim 1, wherein a median particle size $Dv_{50}$ of the terephthalic acid crystals is in a range of 70-150 μm.

* * * * *